United States Patent [19]
Ravetch et al.

[11] Patent Number: 5,116,965
[45] Date of Patent: May 26, 1992

[54] METHODS OF OBTAINING HISTIDINE-RICH PROTEIN GENES OF PLASMODIA, AND DNA OBTAINED THEREFROM

[75] Inventors: Jeffrey V. Ravetch; Laura Pologe, both of New York, N.Y.

[73] Assignee: Sloan-Kettering Institute For Cancer Research, New York, N.Y.

[21] Appl. No.: 900,401

[22] Filed: Aug. 26, 1986

[51] Int. Cl.$^5$ .................... C07H 21/04; C07K 13/00; C12Q 1/68; G01N 33/68

[52] U.S. Cl. ........................................ 536/27; 435/6; 435/69.1; 435/91; 435/172.3; 435/814; 435/849; 436/501; 530/358; 530/802; 530/825; 935/12; 935/18; 935/19; 935/29; 935/47; 935/55; 935/72; 935/78

[58] Field of Search .................... 435/6, 91, 70, 172.3, 435/814, 849; 436/501; 530/358, 825, 802; 536/27; 935/12, 18, 19, 29, 47, 55, 72, 73, 78

[56] References Cited

PUBLICATIONS

Ravetch et al. (1984) Nature vol. 312, pp. 616–620.
Wallach et al. (1984) *Molecular and Biochemical Parasitology*, vol. 12, pp. 85–94.

*Primary Examiner*—Esther L. Kepplinger
*Assistant Examiner*—Ardin H. Marschel
*Attorney, Agent, or Firm*—John P. White

[57] ABSTRACT

A method for obtaining DNA expressing histidine rich protein of various types of Plasmodia is disclosed. The method involves hybridization with the comparable DNA of *P. lophurae*. The method of particularly well suited for obtaining *P. falciparum* DNA, whether it is associated with know or knobless phenotype. Additionally, the invention disclosed a safe method for diagnosing *P. falciparum* infection.

3 Claims, 22 Drawing Sheets

 FcR-3
 A-2
D-3
D-4
 CDC-1
T-26
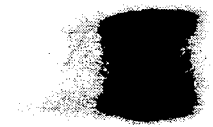 FVO+
FVO−
Human
FIGURE 1B

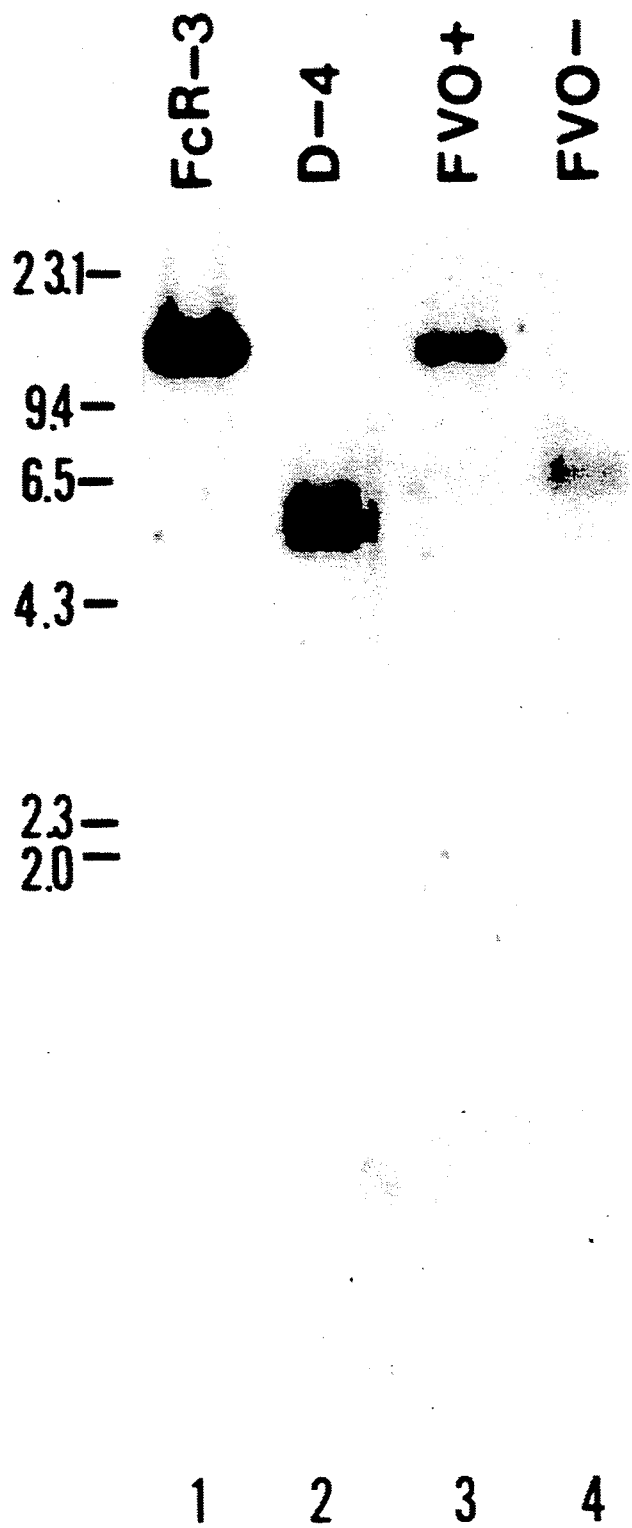

```
TAAATAATAATATATATATTTTTTTAATTTTTTATAGAAATTTCCTTTTTTTTATATATTCTAATATATA
         10        20        30        40        50        60        70
CATAATATATATTTATTATAGATATTTATACATAATGTAATTTATTGTAATATATATTAATCTTTTTTAT
    85        95        105       115       125       135       145
TTTTTATTATATATATAAAAAAATATTTTATGATATTTTTGCTGAAAACAAGATTGAAAATAGAAAAT
    160       170       180       190       200       210       220
TTTATATAATGAGAAAAATTAGAATTCACTTAAGAATTATTATATTTTTTTATATAAATTTTTTTTT
    235       245       255       265       275       285       295
TTTTTTAATTTATATTATTGTTTTAGAATACATTTTTTGTATAAAATTTTTCATATATATACATATTTT
    310       320       330       340       350       360       370
GTTTTATATAATTTTTTATAATATACAATATATATTATTTTATATGTTTATTAACACATTTTTT
    385       395       405       415       425       435       445
TTATATTCATTATTATATTGGTTTTTTTTTTTTTTTTTTATAAATATAACATATATTAGTTATT
    460       470       480       490       500       510       520
TTTTACACCTAAAGAAAAATATAATTATTTTTAAAGGAAAAGTATTATAAAGAAAACAATATATTATATATT
    535       545       555       565       575       585       595
TTACAAAATTATATATTCGTACATAATTATTAGAGAATGAAAAGTTTTAAGAACAAAATACTTTGAGGAGAAA
    610       620       630       640       650       660       670
              M  K  S  F  K  N  K  N  T  L  R  R  K
TTACAAAATTATATATTCGTACATAATTATTAGAGAATGAAAAGTTTTAAGAACAAAATACTTTGAGGAGAAA
    610       620       630       640       650       660       670
 K  A  F  P  V  F  T  K  I  L  L  V  S  F  L  V  W  V  L  K  C  S  N  N  C
GAAGGCTTCCCTGTTTTTACTAAAATTCTCTTTTTTAGTCTCTCTTTTTTAGTATGGGTTTTGAAGTGCTCTAATAACTG
    685       695       705       715       725       735       745
```

FIGURE 4B

```
N  N  G  N  G  S  G  D  S  F  D  F  R  N  K  R  T  L  A  Q  K  Q  H  E  H
CAATAATGGAAACGGATCCGGTGACTCCTTCGATTTCAGAAATAGAGAACTTTAGCACAAAGCAACATGAACA
         760              770         780        790        800         810        820

H  H  H  H  H  Q  H  Q  H  Q  H  Q  A  P  H  Q  A  H  H  H  H  H  H  G
CCATCACCACCATCACCATCAACATCAACACCAACCAAGCTCCACACCAAGCACACCACCATCATCATCATGG
         835            845         855        865        875        885          895

E  V  N  H  Q  A  P  Q  V  H  Q  Q  V  H  G  Q  D  Q  A  H  H  H  H  H
AGAAGTAAATCACCAAGCACCACCAGGTTCACCAACAGTACATGGTCAAGACCAAGCACACCACCATCACCATCA
         910          920         930        940        950        960         970

H  H  H  Q  L  Q  P     Q  L  Q  G  T  V  A  N     P  S  N  E  P  V  V  K
CCACCATCATCAATTACAACCTCAACAACTCCAGGGAACAGTTGCTAATCCTCCTAGTAATGAACCAGTTGTAAA
         985          995       1005       1015       1025       1035      1045

T  Q  V  F  R  E  A  R  P  G  G  G  F  K  A  Y  E  E  K  Y  E  S  K  H  Y
AACCCAAGTATTCAGGGAAGCAAGACCAGGTGGAGGTTTCAAAGCATATGAAGAAAATACGAATCAAACACTA
        1060       1070       1080       1090       1100       1110        1120

K  L  K  E  N  V  V  D  G  K  K  D  C  D  E  K  Y  E  A  A  N  Y  A  F  S
TAAATTAAAGGAAAATGTTGTCGATGGTAAAAAGATTGTGATGAAAAATACGAAGCTGCCAATTATGCTTTCTC
       1135        1145       1155       1165       1175       1185        1195

E  E  C  P  Y  T  V  N  D  Y  S  Q  E  N  G  P  N  I  F  A  L  R  K  R  F
CGAAGAGTGCCCATACACCGTAAACGATTATAGCCAAGAAAATGGTCCAAATATTTGCCTTAAGAAAAGATT
        1210       1220       1230       1240       1250       1260        1270
```

FIGURE 4C

```
           P  L  G  M  N  D  E  D  E  E  G  K  E  A  L  A  I  K  D  K  L  P  G  G  L
CCCTCTTGGAATGAATGATGAAGATGAAGAAGGTAAAGAAGCATTAGCAATAAAAGATAAATTACCAGGTGGTTT
       1285         1295         1305         1315         1325         1335         1345

D  E  Y  Q  N  Q  L  Y  G  I  C  N  E  T  C  T  T  C  G  P  A  A  I  D  Y
AGATGAATACCAAAACCAATTATATGGAATATGTAATGAGACATGTACCACATGTGGACCTGCCGCTATAGATTA
       1360         1370         1380         1390         1400         1410         1420

V  P  A  D  A  P  N  G  Y  A  Y  G  G  S  A  H  D  G  S  H  G  N  L  R  G
TGTTCCAGCAGATGCACCAAATGGCTATGCTTATGGAGGAAGTGCACACGATGGTTCTCACGGTAATTTAAGAGG
       1435         1445         1455         1465         1475         1485         1495

H  G  N  K  G  S  E  G  Y  G  Y  E  A  P  Y  N  P  G  F  N  G  A  P  G  V
ACACGGTAATAAAGGTTCAGAAGGTTATGGATATGAAGCTCCATATAACCCAGGATTTAATGGTGCTCCTGGAGT
       1510         1520         1530         1540         1550         1560         1570

M  V  C  K  L  C  P  T  P  W  C  R  L  F  S  S  I  R  S  S  T  W  C  S  H
AATGGTATGCAAATTATGTCCCCACCCCATGGTTGCAGGCTATTCAGCTCCAGCTCCATACGGAGTTCCACATGTGCAGCCA
       1585         1595         1605         1615         1625         1635         1645

G  S  R  Y  S  S  F  S  S  V  N  K  Y  G  K  H  G  D  E  K  H  H  S  S  K
TGGTTCAAGATATAGTTCATTCAGTTCCGTAAATAAATATGGAAAACACGGTGATGAAAAACACCATTCCTCTAA
       1660         1670         1680         1690         1700         1710         1720

```
AAAGCATGAAGGAAATACGGTGAAGGAGAGAAAAAGAAAAATCAAAAAGACACAAAGACCACGATGGAGAAAAG
     1735           1745           1755           1765           1775           1785           1795
 R    N    Q    K    N    T    K    T    M    K    M    Q    K    A    *
AAAAAATCAAAAAACACAAAGACAATGAAGATGCAGAAAGCGTAAATCAAAATACACAAAGCCACGATTGT
     1810           1820           1830           1840           1850           1860           1870
GAAAAGAAAAATCAAAAAACACAAAGACACAATGAAGATGCAGAAGCGTAAATCAAAAAAGTGTTAAAGAA
     1885           1895           1905           1915           1925           1935           1945
AAGGGAGAAAAGCATAATGGAAAAAAACCATGCAGCAAAAAACTAACGAAGAAAATAAAATAAGAAAAAACC
     1960           1970           1980           1990           2000           2010           2020
AATAATTTAAAATCAGATGGATCAAAAGCTCATGAAAAAAAAAAAACCCCCCCCCCTGCAGGTCT
     2035           2045           2055           2065           2075           2085           2095
GCAG
     6          16          26          36          46          56          66
```

FIGURE 7A

```
                                                                                                    71
GAATTCTATTATTAAACTTATTAAATATATATTTCTTTTAAAGAAATATTTATTCATTTTTAGTTTT

142
TTTAAACATTTTTTTTTTTTTTTTGATAAATAAATATCCATTCTAAGGCAACTGCTGTTTATTTT

213
AAGATAAACAATATATTTATATCTTAAAATTACCATAATTAACAATGGATTCATCAATGCCAACAATA

284
ATATTAGGATTTCCAATGAGGAGGTCATGCGGCCACAACAGCCCTTAAATCAAATCAAAAAAGGAAA
            -47  Met Phe Thr Ser Leu Lys Lys Val Ala Thr Phe Ser Phe Leu Val Trp
                                                                                                   338
GGAAGT ATG TTT ACT TCT CTT AAG AAA GTT GCT ACT TTT TCC TTT CTA GTT TGG
       -40
Ile Ser Gln Tyr Gly Ser▽
                    -25                                                                            402
ATA TCT CAA TAT TCA GGA AGC GTAAG TAAAGCTAATAATATAAAAATTATATATGTTATGTTT

473
TTCTTATTTTACATACTTTAAATAAAATGATAATAAAAAGAAAATCTTTAACATTTAATT
                   -24
       Asn Ser Cys Ser Ser Leu Val Lys His Ile Pro Gln
       AAT TCA TGT AGC TCC TCA CTT GTC AAA CAT ATC CCA CAA                                          529
                                 -1▼1
TTTTATTTATA NTATAG
         -10
Thr Gly Ser Asn Leu Thr Phe Asp Arg Val Leu Val Glu Asp Thr Val His Pro
ACG GGG TCA AAC TTA ACA TTT GAT AGA GTT TTA GTA GAA GAT ACA GTA CAC CCT                            583
 10                                       20
Glu His Leu His Glu Glu His His His His His Pro Glu His His Glu Pro
GAA CAT CTC CAT GAA GAA CAT CAC CAT CAT CAT CCC GAG CAT CAT GAA CCA                                637
             30                                 40
His His Glu Glu His His His His His Pro Glu Glu His Glu Pro His His
CAT CAT GAA GAA CAT CAC CAT CAT CAC CCT GAG CAT GAA CCA CAT CAT                                    691
                 50                                        60
Glu Glu His His His His Leu Gly His His His His His His His His Pro
GAA GAA CAT CAT CAT CAC CTA GGA CAT CAT CAT CAT CAT CAT CAT CAT CCT                                745
                         70
Pro His His His His Glu Glu His His His His His-CAT Ala Ala His His
CCT CAT CAT CAT CAT GAA GAG CAT CAC CAT CAT CAT.CAT GCA GCA CAT CAT                                799
80                                            90
His His His Glu Glu His His His His Ala Ala His His His His His His
CAC CAT CAT CAT GAA GAG CAT CAC CAC GCA GCA CAT CAT CAT CAC CAT CAC                                853
                 100                                   110
His Glu Glu His His His His Ala Ala His His His Pro Trp Phe His
CAC GAA GAG CAT CAT CAC CAT CAT GCA GCA CAT CAT CAT CCA TGG TTT CAC                                907
```

```
                                                                                          120                                                                        130
His His Leu Gly Tyr His His His Ala Pro His His His His His His His His                                             961
CAC CAT TTA GGA TAT CAC CAT CAC GCT CCA CAT CAC CAT CAC CAT CAC CAT CAT
                140                                 150

His His Ala Pro His His His Ala Pro His His His His Ala Pro His His His                                            1015
CAC CAT GCT CCA CAC CAT CAT GCT CCA CAC CAC CAT CAT GCT CCA CAC CAT CAC
        160

His His His His Ala Pro His His His His His His His His Ala Pro His His                                            1069
CAC CAC CAT CAT GCT CCA CAC CAC CAT CAC CAC CAT CAC CAT GCT CCA CAC CAT
170                                     180

His His His Gly His His His His His His His His Gly His His His Gly His                                            1123
CAT CAC CAT GGT CAC CAT CAC CAC CAT CAC CAC CAT GGT CAC CAT CAC GGT CAC
        190                                     200

His His His His His His His His His His His His His His His His His His                                            1177
CAC CAT CAT CAC CAC CAC CAT CAC CAC CAT CAC CAC CAT CAT CAC CAC CAT CAT
210                                     220

Asp Ala His His His His His Asp Ala His His His His His His His His His                                            1231
GAT GCA CAC CAC CAC CAC CAT GAT GCA CAC CAC CAC CAC CAT CAT CAC CAC CAT
        230                                     240

His His Asp Ala His His His His His Asp Ala His His His Asp Ala His His                                            1285
CAT CAC GAT GCA CAT CAC CAC CAC CAT GAT GCA CAC CAC CAC GAT GCA CAC CAC
250

His His His His His Asp Ala His His His His His Asp Ala His His His His                                            1339
CAT CAT CAC CAC CAC GAT GCA CAT CAC CAC CAT CAC GAT GCA CAT CAC CAC CAC
260                                     270

His His His His His Asp Ala His His His His His His His His His Asp                                                1393
CAC CAC CAT CAT CAC GAT GCA CAC CAT CAC CAT CAC CAC CAC CAT CAT CAC GAT
        280                                     290

His His His His His His His His His His His His His His His His His His                                            1447
CAC CAC CAT CAT CAC CAT CAC CAT CAC CAT CAC CAC CAC CAC CAT CAT CAC GAT
                300

Ala His His His His His His
GCA CAC CAC CAC CAC CAT CAC TAATGGGTTCACCAAGACATCACTCTTAAGGGGTG           1509

TTATGTGAATTTATTTAAATAGAATAGCATTTATATATATATATATATATATGCAAATACAT           1580

TACGTAGACTATTTTTACTGTTAATCTTTATTCCAGTGATTCCATTTCTTCATTATTCAATGATC        1648
```

ATTAGGATTCCAATGAGGAGGTCATGCGGCCACAACAGCCTTAAATCAAATCAAAAAAGGGAAAG

Met Phe Thr Ser Leu Lys Lys Val Ala Thr Phe Ser Phe Leu Val Trp
GAAGT ATG TTT ACT TCT CTT AAG AAA GTT GCT ACT TTT TCC TTT CTA GTT TGG

Ile Ser Gln Tyr Ser Gly Ser
ATA TCT CAA TAT TCA GGA AGC

METHODS OF OBTAINING HISTIDINE-RICH PROTEIN GENES OF PLASMODIA, AND DNA OBTAINED THEREFROM

FIELD OF THE INVENTION

This invention relates to a method of using DNA probes, and cDNA obtained from the use of these. Specifically, it relates to the use of a probe of DNA from *Plasmodium lophurae* which is used to obtain equivalent cDNA from other strains of Plasmodia. Specifically *Plasmodium falciparum* histidine-rich protein expressing DNA. The cDNA thus obtained is claimed as well.

BACKGROUND AND PRIOR ART

*Plasmodium lophurae* is a protozoan parasite and is the causative agent of malaria in birds. Like all strains of Plasmodia, it has a complex life cycle which has been studied in some detail. See, e.g., Aikawa, *Exp. Parasitol* 30:284-320 (1971); Aikawa et al., *J. Cell. Biol.* 77:72-82(1972).

During the intraerythrocytic stages of development of *P. lophurae*, synthesis of a major protein occurs which eventually accumulates to comprise at least 50% of the cellular mass of the parasite. This protein is a basic polypeptide of about 45 kilodaltons, and is comprised of about 73% histidine. It is referred to as the "Histidine Rich Protein (HisRP). In this regard, see Kilejian, *J. Biol. Chem.* 249:4650-4655 (1974).

Recently, the gene expressing *P. lophurae* HisRP has been cloned. Ravetch et al., *Nature* 312:616-620 (1984). The disclosure of the Nature paper is incorporated by reference herein.

Due to the similarity in life cycles of different strains of Plasmodia, it was thought that possibly analogous HisRP was produced by other strains of Plasmodia responsible for malaria in other species. In particular, *Plasmodium falciparum*, the causative agent of malaria in humans, was studied.

It has been learned that a HisRP is in fact produced by *P. falciparum*, and that two variants are produced. One is associated with what is referred to as "knobby phenotype" ($K^{30}$); Kilejian, *Proc. Natl. Acad. Sci.* 76:4650-4653 (1979); and "knobless phenotype" ($K^-$); Schmidt et al. *J. Clin. Invest.* 70:379-386 (1982). The "knobby" and "knobless" phenotypes have been implicated in cytoadherence, which is characteristic of erythrocyte infection. Trager et al. *Bull. W.H.O.* 35:883-885 (1966); Luse et al., *Am. J. Trop. Med. Hyg.* 20:655-660 (1971).

It has now been found that cDNA expressing both $K^+$ and $K^-$ HisRP can be obtained by the use of *P. lophurae* HisRP expressing DNA. The implication of such a discovery are of great interest and value to those in the art, as will be evident from review of the disclosure which now follows.

BRIEF DESCRIPTION OF THE FIGURES

FIG. 1B depicts the results of hybridization experiments using radiolabelled $K^+$ cDNA with various geographically isolated strains.

The combined FIGS. of 4A, 4B, 4C, and 4D show the DNA sequence of $K^+$ cDNA, with accompanying amino acid sequence expressed by this cDNA.

Figure 5A:
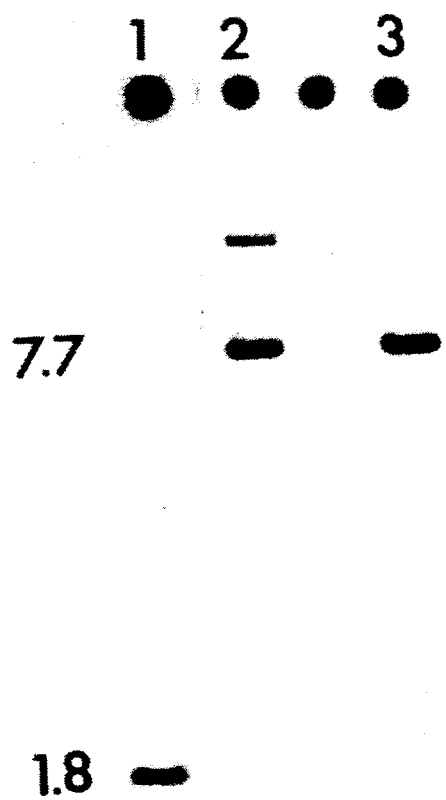
Figure 5B:
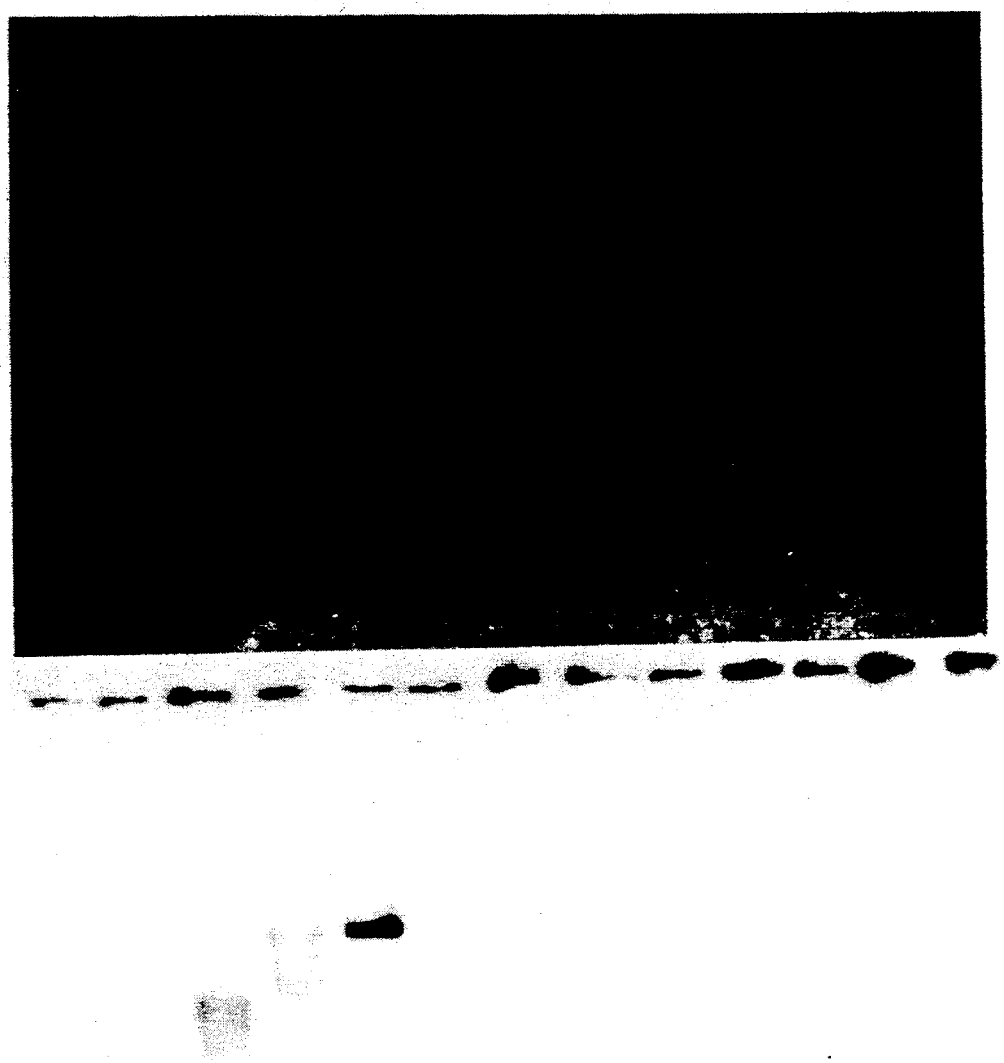

FIG. 5A and 5B: Genomic cloning of the HisRP gene into λL47.1. (5A) *P. lophurae* DNA was isolated from infected duck erythrocytes by the saponin lysis procedure as described (Sherman, I. W. *Exp. Parasitol*, 52, 292-295 (1981); Blin, N. and Stafford, D. W. *Nuc. Acids Res.* 3, 2303-2308 (1976)). 2 micrograms of high molecular weight DNA were digested with Eco RI (lane 1) or Hind III (lane 3). The resulting fragments were separated on a 0.75% agarose gel and transferred to nitrocellulose paper as (Southern, E. J., *Mol. Biol* 98, 503-517(1975)). The gel was probed with nick-transferred HisRP cDNA labelled to a specific activity of $2 \times 10^8$ cpm/microgram and hybridized in 50% formamide, 10% dextran sulfate, 5×SSC, 1×Denhardt's, 200 microgram/ml of salmon sperm DNA at 40° C. for 16 hours. Non-specific hybridization was washed off in 0.1×SSC, 0.1% SDS at 54° C. and the filters were exposed to Kodak XAR film with Dupont Lightening Plus intensifying screens at $-70°$ C. for 4-16 hours. The specific 1.8 kb Eco RI and 7.7 kb Hind III fragments which hybridize to the cDNA probe are indicated. Lane 2 contains the DNA isolated from clone 8A, digested with Hind III and coelectrophoresed with *P. lophurae* DNA demonstrate that an intact fragment had been cloned. 5B Preparative agarose electrophoresis of *P. lophurae* DNA to enrich for the 7.7 kb Hind III fragment containing the HisRP gene. 100 micrograms of *P. lophyrae* DNA were digested to completion with Hind III and fractionated on a Bulls Eye Electrophoresis apparatus (Hoefer Scientific). Fractions were collected, and aliquots analyzed on a 0.75% agarose gel shown in the upper panel. The DNA fragments were transferred to nitrocelulose paper and probed with the HisRP cDNA probe. A peak fraction containing the 7.7 kb Hind III fragment is visible in the lower panel. This fraction was ligated into λL47.1 Hind III arms, packaged in vitro (Scalenghe, et al. *Chromosoma* 82, 205-216 (1981)) and used to infect LE 392. $1 \times 10^5$ recombinant phage were obtained from a microgram of *P. lophurae* DNA. $5 \times 10^4$ phage were screened by in situ hybridization (Benton, W. D. and Davis, R. W. *Science* 196, 180-182 (1977)) with the nick-translated cDNA probe. A positive obtained, referred to as 8A, was plaque purified. DNA isolated from this phage was mapped against *P. lophyrae* DNA as seen in panel A, lane 2 and as described in the text.

Figure 6:
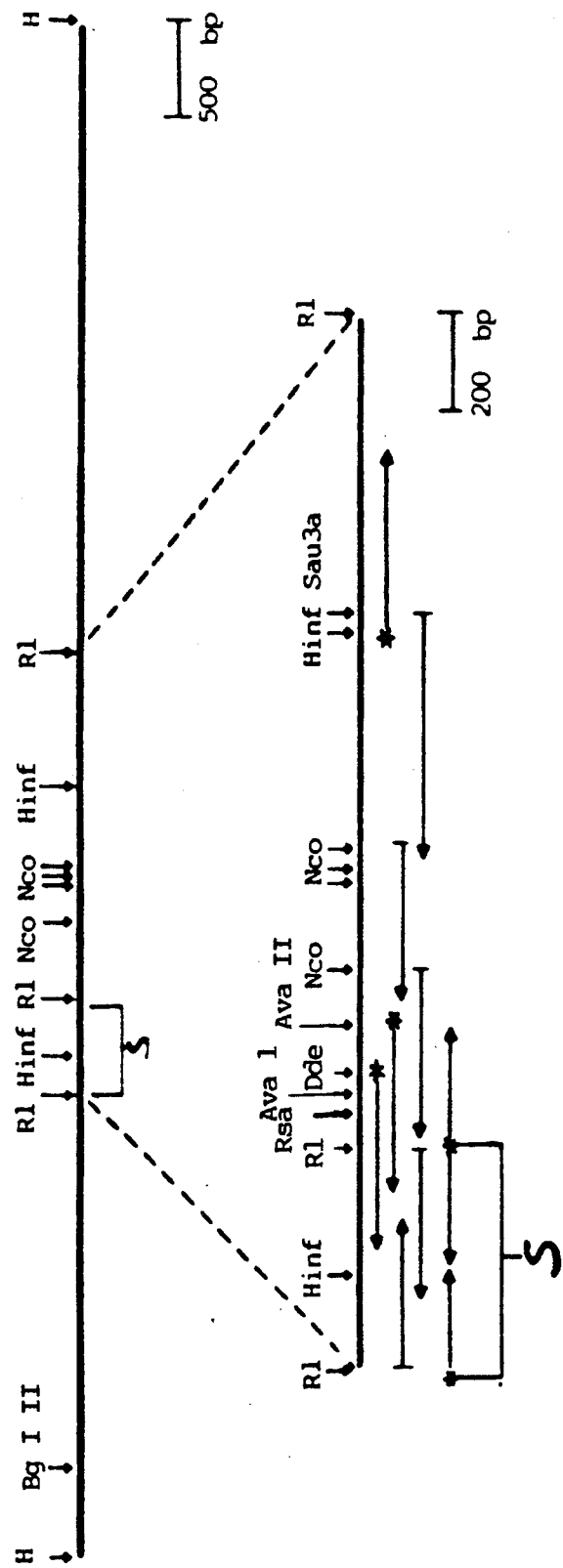

FIG. 6: Restriction map analysis and sequencing strategy for clone 8A of the histidine-rich protein gene. The 7.7 kb Hind III fragment, cloned as described in brief description of FIGS. 5A and 5B, was mapped both within the phage and from a pBR322 subclone. Fragment sizes of the clones DNA were compared with *P. lophurae* DNA. DNA sequencing analysis was performed using both the dideoxy method of Sanger and Coulson, *J. Mol. Biol.* 94, 441-448 (1977) indicated by arrows ending with vertical lines, and by the chemical method of Maxam and Gilbert, *Proc. Natn. Acad. Sci. U.S.A.* 74, 560-564 (1977), indicated by arrows ending with stars. Fragments were obtained both from phage clone 8A and from the pBR322 subclone. Repeat sequences obtained with the same fragment or M13 clone are not shown. The sequence obtained from the 3' Hinf site to the 5 Nco site was derived from two M13 clones which could be obtained in only one orientation due to the instability of the sequences in *Escherichia coli*. Multiple independent isolates of these clones were sequenced to generate the data shown in FIGS. 7A and 7B. This overlap, however, may be subject to some ambiguity.

FIGS. 7A and 7B: Nucleotide sequence of the gene for histidine-rich protein and the predicted amino acid sequence of the preproprotein protein and the predicted amino acid sequence of the preproprotein. 1,648 nucleotides are shown, corresponding to the region indicated in FIG. 6. The predicted amino acid sequence is numbered beginning at −47 for the signal peptide and at −24 for the pro-peptide. The mature protein begins at amino acid 1 and corresponds to the N-terminal amino acid sequence obtained by Howard, et al. (in press) ∇/, A potential signal peptidase cleavage site (Perlman, D. and Halvorson, H. O., *J. Mol. Biol.* 167, 391–409 (1983); Von Heijne, G. *Eur. J. Biochem.* 133, 17–21 (1983)) ∇, the processing site between the proprotein. A potential site for Asn-linked glycosylation in the pro-peptide portion is overlined. The 5' and 3' putative splice sequences.

Figure 8:
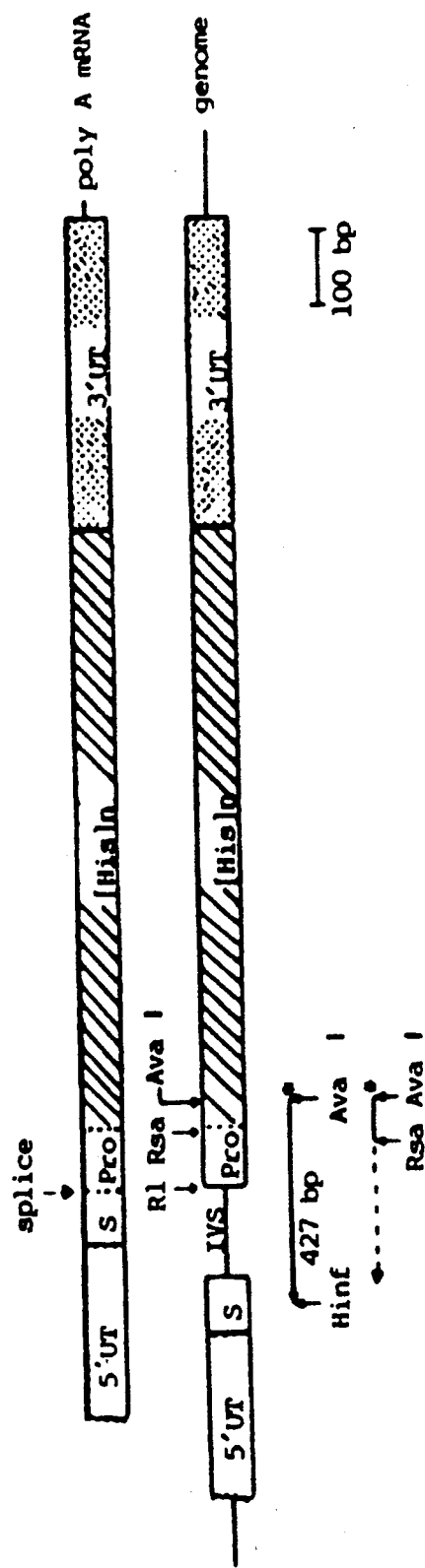

FIG. 8: The organization of the ghistidine-rich protein DNA, mRNA and the expressed protein. A schematic representation of the gene and its transcript are shown with the intervening sequence (IVS) indicated in the gene. The protein is divided into a pre (signal) sequence, a pro-peptide and mature protein. Transcribed and untranslated (UT) sequences are indicated. The precise 5' initiation site of the mRNA has not been determined and is indicated by the sawtooth line at the 5' end of the DBNA and mRNA. A 427-bp AvaI-Hinf fragment derived from the genomic clone 8A is indicated, as is a 42-bp AvaI-Rsa fragment used in the primer extension studies described in the text. The fragments were derived from the non-coding strand and were 5' end-labelled.

Figure 9A:
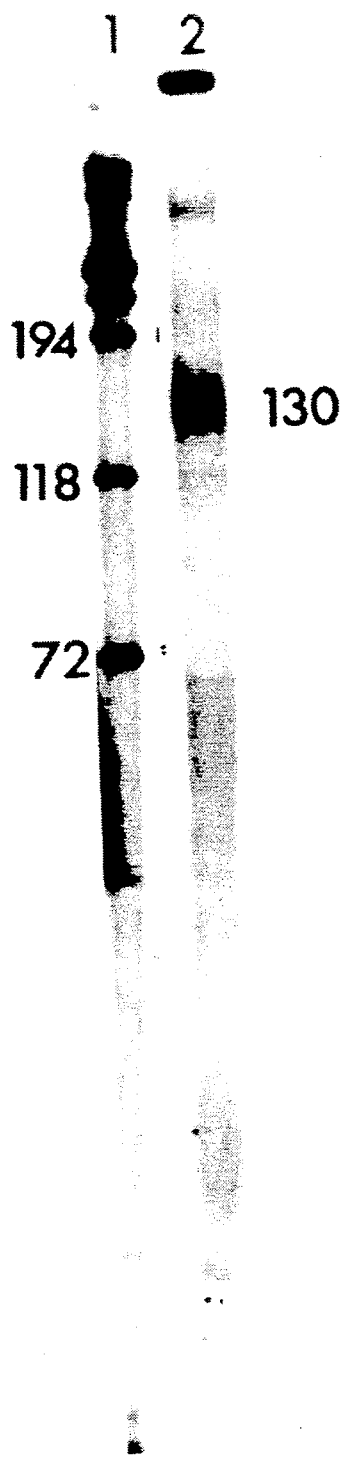
Figure 9B:
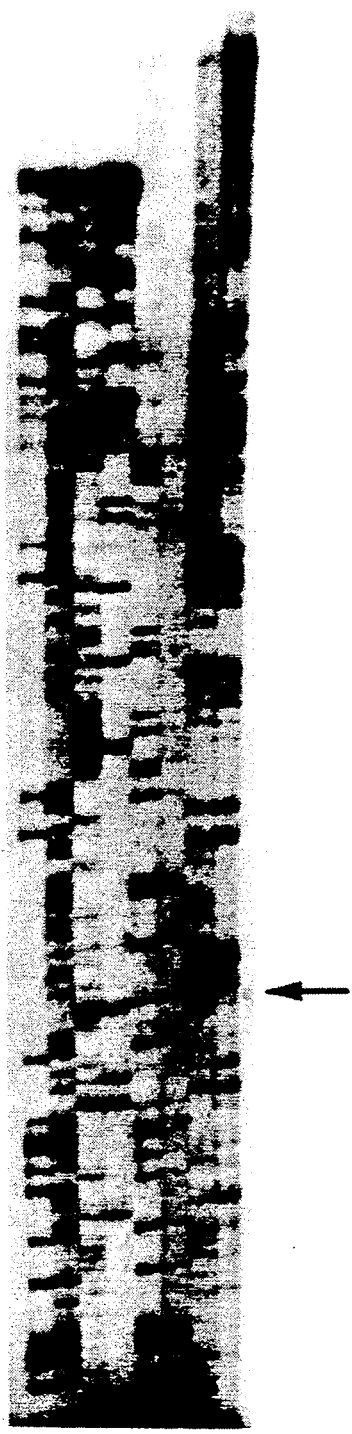

FIGS. 9A, 9B, and 9C: Mapping the intron in the gene for histidine-rich protein. $S_1$ (FIG. 9A) nuclease mapping; (FIG. 9B), primer extension, Lane 1, an autoradiogram of the DNA sequencing gel for the genomic AvaI-Hinf fragment; lane 2, the primer-extended fragment. (FIG. 9C), cDNA sequence of the 5' exon and untranslated region deduced from the primer-extension experiment in (FIG. 9B) in b. The predicted amino acid sequence is shown above the nucleotide sequence, identical to the genomic sequence in FIG. 7A and 7B. The sequence beyond the break point is shown, corresponding to the 5' exon sequence. (Identical 3' sequences for the two fragments are not shown.). a, A 427-bp AvaI-Hinf fragment, spanning the intron-exon border, was isolated (see FIG. 8), labelled on the 5' AvaI end and strand-separated on a 10% polyacrylamide gel. $2 \times 10^4$ c.p.m. were co-precipitated with 10 μg of *P. lophurae* mRNA in 70% ethanol at −20° C. for 16 h. The precipitate was resuspended in 30 μl of 80% formamide, 0.4 M NaCl, 40 mM PIPES, pH 6.4 and 1 mM EDTA. The reaction was incubated at 80° C. for 15 min, rapidly cooled to 50° C., then incubated at 50° C. for 3 h. The reaction was diluted with 0.3 ml of $S_1$ buffer (0.28 M NaCl, 0.05 M NaAc, pH 4.5, 4.5 mM $ZnSO_4$) and 300 units of nuclease $S_1$ were added. The reaction was incubated for 30 min at 37° C. and stopped by adding 10 μl 0.5 M EDTA. After phenol-chloroform extraction, the $S_1$ nuclease-resistant material was ethanol-precipitated, resuspended in 95% formamide and dyes and fractionated on a 10% acrylamide, 7M urea sequencing gel. The gel was dried and autoradiographed for 16 h. Size markers (lane 1) are indicated, as is the position of the protected DNA fragment at 130 nucleotides (lane 2), b, A 42-bp AvaI-Rsa fragment was labelled on the Ava I end, strand-separated and coprecipitated with 10 μg of *P. lophurae* mRNA in 70% ethanol at 20° C. for 16 h. The pellet was resuspended in 50 μl of 0.1 M NaCl, 1 mMEDTA, 10 mM Tris, pH8.3. An extension reaction of 100 μl volume containing 50 mM t=Tris pH 8.3, 10 mM $MgCl_2$ 1 mM of each of the four DNTPs, 10 mM dithiotreitol and 100 units of reverse transcriptase was incubated at 42° C. for 1 h and terminated by the addition of EDTA to 10 mM, followed by phenol extraction and ethanol precipitation. The pellet was resuspended in formamide-dye loading buffer and fractionated on a 10% DNA sequencing gel. The resulting 600-nucleotide fragment was eluted from the gel and subjected to DNA sequencing by the method of Maxam and Gilbert *Proc. Natn. Acad. Sci. U.S.A.* 74, 560–564 (1977). The arrow indicates the break point of the two sequences, which corresponds to the intro-exon junction (see FIG. 7).

DETAILED DESCRIPTION OF PREFERRED EMBODIMENTS

*P. lophurae* Probes

The protozoan parasite *Plasmodium lophurae* causes malaria in birds, invading host erythrocytes via a mechanism which involves specialized intracellular parasite organelles and surface receptors on both the parasite and the erythrocyte (Aikawa, M. *Exp. Parasitol*, 30, 284–320 (1971); Aikawa, et al. *J. Cell. Biol.* 77, 72–82 (1972); Miller, et al. *Am. J. Trop. Med. and Hyg.* 26, 204 (1977); Perkings, M. *J. Cell. Biol.* 90, 563–567 (1981)). Recognition and binding of the two cells is followed by complete engulfment of the protozoan cell by the erythrocyte, whereupon the parasite undergoes several rounds of asexual divisions. Mature daughter cells escape from their intraerythrocytic confinement to begin a new round of erythrocyte invasion. In the intraerythrocytic stages of development of *P. lophyrae* in ducks, there is synthesis of a major protein that accumulates to comprise at least 50% of the cellular mass. This protein, a basic polypeptide of relative molecular mass ($M_r$) 45,000 comprising 73% histidine, is located in a membrane-bounded compartment that forms part of the specialized parasite organelles implicated in erythrocyte invasion. (Kilejian, A. *J. Biol. Chem.* 249, 4650–4655 (1974)). The function of the protein is unknown. In one series of experiments, antibodies to this protein were found to be protective, (Kilejian, A. *Science* 202, 922–924 (1978)), but other investigators have been unable to reproduce these results (McDonald, et al. *Exp. Parasitol*, 51, 195–203 (1981); Sherman, I. W. *Exp. Parasitol*, 52, 292–295 (1989)).

We have shown that the early biosynthetic forms of the histidine-rich protein resemble those of secretory proteins (Feder, R. and Bolbel, G. *Mol. Biochem. Parasitol.* 9, 351–362 (1983). Translation of parasite mRNA in a cell-free wheat-germ translation system yielded a larger precursor that was translocated into dog pancreas microsomal membrane vesicles. The segregated form was larger than the mature protein and contained Asn linked oligosaccharide (Feder, R. and Bolbel, G.

*Mol. Biochem. Parasitol.* 9, 351-362 (1983). These data suggested that the histidine-rich protein is synthesized as the preproprotein containing two transient sequences, a pre-sequence that functions as a signal sequence for translocation across the rough endoplasmic reticulum, and a glycosylated prosequence of unknown function.

We have now isolated a genomic clone that contains the entire histidine-rich protein gene and have determined its DNA sequence. The gene is encoded in two exons, separating the signal peptide-encoding sequence from the pro-sequence, confirming that synthesis of the protein occurs via the preproprotein. Oligonucleotide probes synthesized to the signal peptide-encoding exon reveal multiple homologous DNA sequences in the *P. lophurae* genome. The sequence of mature proteins is arranged in numerous tandem repeats with up to nine histidine residues in a row, similar to other Plasmodium proteins for which sequence data have so far been reported (Ozaka, et al. *Cell* 34, 815-822 (1983); Coppel, et al. *Nature* 306, 751-756 (1983); Dame, et al. *Science* 225, 593-599 (1984); Enea, et al. *Science* 225, 628-629 (1984); Coppel, et al. *Nature* 310, 789-792 (1984); Koenen, et al. *Nature* 31, 382-385 (1984)).

Genomic Clone Isolation

A partial cDNA clone, obtained by screening a *P. lophurae* cDNA library with a synthetic oligonucleotide encoding a polyhistidine sequence (Wallach, M. and Boeke, J. D. *Proc. Natn. Acad. Sci. U.S.A.* 80, 1867-1871 (1983)) was used to determine the genomic organization of the HisRP. As shown in FIG. 5A, *P. lophurae* DNA digested with Hind III (lane 3) or Eco RI (lane 1) and probe with a HisRP cDNA probe detected a 7.7 kg and 1.8 kb fragment, respectively. The 7.7 kg Hind III fragment was cloned into the phage λL47.1 Hind III arms by enriching Hind III digested *P. lophurae* DNA by preparative agarose electrophoresis as shown in FIG. 5B. Screening of 50,000 recombinant phages with the HisRP cDNA probe yielded a positive clone identified as 8A. Propagation of 8A in Le 392 resulted in spontaneous deletion of the cloned insert leading to segregation of the phage into two populations separable on CsCl density gradients. Only higher density, full length phage particles were used for subsequent studies. As seen in FIG. 5A, Hind III digestion of clone 8A (lane 2) yielded a 7.7 kb fragment which comigrated with the genomic Hind III fragment (lane 3) detected with the HisRP cDNA probe. No deletion was apparent in this higher density phage fraction. The 7.7 kb Hind III fragment conaining the HisRP genomic sequence was subcloned into pBR 322 and propagated in LE 392. Spontaneous deletion of the insert occurred in this system as well. A subclone 8 A-1 showed a 3.0 kb deletion in the 3' Eco RI-Hind III fragment of clone 8A. Detailed restriction endonuclease mapping of clone 8A and subclone 8A-1 are shown in FIG. 6. To confirm that no deletion or rearrangement had been introduced in the region containing the His RP gene by the cloning procedures, additional restriction map comparisons were performed. Eco RI digests of clone 8A, 8A-1 and *P. lophurae* DNA revealed a co-migrating 1.8 kg fragment when probed with the cDNA probe (data not shown). Bgl II - Nco I digests of these DNAs revealed co-migrating 2.85 kg and 200 bp fragments when probed with the 1.8 kb Eco RI fragment. These data confirm that no deletion or rearrangement had occurred in the 7.7 kb Hind III fragment in clone 8A or in the sequences extending from the Bgl II site 5' of the gene to the Eco RI site 3' of the gene in the subclone 8 A-1.

Gene Structure

The DNA sequencing strategy for the region encoding the HisRP is shown in FIG. 6. The determined sequence comprised 1648 nucleotides shown in FIG. 7A/7B. An open reading frame extended from nucleotide 491 to nucleotide 1487. Of the 328 amino acids coded for by this open reading frame, 225 residues are histidine. 24 amino acids within this reading frame (beginning at nucleotide #563), there is a sequence that is identical to the recently reported sequence of 25 $NH_2$ terminal residues of mature HisRP (Howard, et al. (in press)). However, there was no methionine in this reading frame, suggesting that the HisRP gene was interrupted and that the amino terminal portion of HisRP was located on another exon(s). Further analysis revealed another open reading frame with a putative initiation codon located at nucleotides 291-293. This open reading frame of 23 amino acids ended in a stop codon (nucleotide 375-377), immediately followed by a splice sequence AAGCGTAAG, (boxed in FIG. 7A.) similar to the consensus 5' splice sequence AAGGTAAG (Breathnach, R. and Chambon, P. A. Rev. Biochem.50, 349-409 (1981)) Similarly, a 3' splice sequence TTATAG, (boxed in FIG. 7A similar to the consensus 3' splice sequence TTXCAG is found immediately adjacent to the next exon. The following experiments were designed to establish the existence of the predicted intron and to establish its precise borders.

To demonstrate that the genomic DNA is not contiguous with its mRNA, S1 nuclease mapping was performed. A 427 bp AvaI-Hinf I fragment (FIG. 8) spanning the intron-exon border was 5' end-labeled on the non-coding strand. After strand separation, the 5' labeled strand was annealed to *P. lophurae* rNA. As shown in FIG. 9a lane 2, S1 nuclease treatment of this hybrid yielded a 130 bp protected fragment, consistent with a discontinuity between the RNA and the genomic DNA at nucleotide 491, at the intron-exon border.

To identify the break point between the DNA and RNA sequences specifically, primer extension studies were carried out. A 42 bp AvaI-Rsa fragment (FIG. 8) was labeled on the 5' end of the non-coding strand. After strand separation, the 5' labeled strand was annealed to *P. lophurae* RNA. A cDNA was synthesized in the presence of dXTPs and reverse transcriptase and the resulting 600 bp fragment was isolated and sequenced by chemical degradation. Parallel sequences were obtained from a 427 bp AvaI-Hinf fragment labeled at the AvaI 5' end. The results of these experiments are shown in FIG. 9B. The primer extended sequence diverges from the genomic sequence precisely at the position of the putative intron. The sequence derived by primer extension, shown in agrees precisely with the 5' exon sequence. A 5' untranslated sequence can be read from the primer extension experiment for at least 150 nucleotides 5' of the exon which similarly is in agreement with the genomic sequence. Additional S1 mapping studies (data not shown) demonstrate that the 5' untranslated sequence extends for approximately 300 nucleotides beyond the open reading frame for the signal peptide. The precise 5' end of the untranslated mRNA sequence has not been identified. R-loop mapping of the genomic clone and mRNA (data not shown) demonstrates a 1,400 nucleotide R-loop, corresponding to the histidine-rich exon and 3'-untranslated sequences.

Therefore, the length of the 3'-untranslated sequence is deduced to be 400 nucleotides (FIG. 8). The size of the mRNA has been identified by Northern gel analysis to be 2,200 nucleotides (Wallach, M. and Boeke, J. D. Proc. Natn. Acad. Sci. U.S.A. 80, 1867–1871 (1983)), suggesting that the 5'-untranslated sequence is approximately 700 nucleotides long.

Amino Acid Sequence

PreproHisRP contains 351 amino acid residues and, in its unglycosylated for, has an $M_r$ of 49,000. The amino acid sequence is numbered beginning at $-47$ for the signal peptide, at $-24$ for the pro peptide and at $+1$ for the mature protein.

The assignment of the methionine at $-47$ as the initiating methionine of preproHisRP needs to be confirmed by amino acid sequencing of the primary translation product. Our principal argument in support of this assignment is that the 24 residue-long sequence following the methionine at $-47$ is highly characteristic of a signal peptide containing a stretch of hydrophobic residues and two charged residues (Lys $-42$ and Lys $-41$) preceding this hydrophobic stretch. The only other in-frame initiation codon further upstream (nucleotides 199–201) would code for a sequence that is not characteristic for a signal peptide.

The assignment of the signal peptidase cleavage site between residues $-25$ and $-24$ is based on consensus features which have been proposed for this site (Perlman, D. and Halvorson, H. O., J. Mol. Biol. 167, 391–409 (1983); Von Heijne, G. Eur. J. Biochem. 133, 17–21 (1983)). Definitive assignment of this site must await NH$_2$ terminal sequencing of in vitro synthesized HisRP that is segregated by dog pancreas rough microsomes (Feder, R. and Bolbel, G. Mol. Biochem. Parasitol. 9, 351–362 (1983)) and that can be expected to have its signal peptide removed by the dog pancreas microsomal signal peptidase at the correct site (Muller, et al. J. Biol. Chem. 257, 11860–11863 (1982)).

The signal peptide is followed by a pro peptide that shows a consensus glycosylation site at Asn $-8$. HisRP synthesized in a cell-free system and segregated by dog pancreas microsomes was indeed found to be core-glycosylated (Feder, R. and Bolbel, G. Mol. Biochem. Parasitol. 9, 351–362 (1983)). The fact that mature HisRP is not core-glycosylated suggests that the core-glycosylated pro peptide portion is removed somewhere upon transport from the rough endoplasmic reticulum to the membrane-bound granules. There are precedents for the existence of core-glycosylated pro peptides in the synthesis of other secretory proteins, the mature forms of which are not core-glycosylated (Julius et al. Cell 36, 309–318 (1984)). Whether the pro peptide of HisRP is also glycosylated in vivo remains to be shown. The function of the pro peptide portion of HisRP is unknown.

The assignment of the beginning of mature HisRP is based on complete coincidence with the recently reported sequence for 25 NH$_2$ terminal residue of mature HisRP (Howard, et al. (in press)). The most striking feature of the sequence organization of mature HisRP are the randomly repeated elements. The histidine-rich sequence begins at amino acid 12 with a sequence (Glu)$_2$-(HIS)$_5$-Pro-(Glu)$_2$-(His)$_2$-Glu-Pro-(His)$_2$ repeated once. Amino acids 44–76 appear to have a degenerate repeat of the form X-X-(His)$_5$-X-X (His)$_7$ repeated once. This is followed by 2 repeats of the sequence (Ala)$_2$-(His)$_5$-(Glu)$_2$-(His)$_6$-(Ala)$_2$, 5 repeats of the sequence Ala-Pro-(His)$_8$.

On the assumption that there is no trimming at the COOH terminus, the mature HisRP (Mr 43,000) contains 74% histidine residues. The other predominant residues in mature HisRP are Ala, Glu, Pro and Asp. Completely absent are Asn, Arg, Cys, Gln, Ile, Lys, Met and Ser. These data are in close agreement with the previously reported amino acid composition of mature HisRP. The highly unusual amino acid composition is probably responsible for the abnormal migration of HisRP in SDS polyacrylamide gel electrophoresis (Feder, R. and Bolbel, G. Mol. Biochem. Parasitol. 9, 351–362 (1983)).

Site of the 5' Exon

Two synthetic oligodeoynucleotide probes comprising the 5' exon were synthesized. These oligonucleotides were 5' end labeled and used as probes to determine the genomic organization of the 5' exon in the P. lophurae genome. The result of such an experiment is shown in FIGS. 9A, 9B, and 9C. In addition to the expected 0.5 kb Eco RI fragment and the 7.7 kb Hind III fragment (see FIGS. 5A, 5B and 6), multiple DNA fragments are detected with the enzymes chosen to digest the P. lophurae DNA, while only a single DA fragment hybridizes to the HisRP cDNA (see FIGS. 5A and 5B), indicating that the 5' exon sequence is present in multiple copies in the genome.

To determine if any of these cross-hybridizing sequences are closely linked to the HisRP gene, clone 8A and subclone 8A-1 were digested with multiple restriction endonucleases and the resulting fragments transferred to nitrocellulose membrane. No additional DNA fragments were found to hybridize with the oligonucleotide probes (data not shown) establishing that greater than 2.0 kb must separate the signal peptide exon from the cross-hybridizing sequences.

It was determined that P. lophurae histidine rich protein expressing DNA can be used as a probe for obtaining cDNA expressing the corresponding protein in other strains of Plasmodium, especially P. falciparum, the major cause of malaria in humans.

A 1.8 kilobase EcoRI DNA fragment expressing P. lophurae histidine rich protein, as is described in Ravetch et al. Nature 312:616–620 (1984) was used as a probe. This was used against a cDNA library of P. falciparum strain FcR-3 (trophozoite stage). This library constructed in the PstI site of plasmid pUC9, as is described by Kochan et al, Cell 44: (1986). The screening was performed under reduced stringency (i.e., 25% formamide, 10% dextran sulfate, 5×SSC, 71 mM Tris pH 7.6, 1×Denhardts biffer. 25 μg/ml salmon sperm DNA at 40° C, final wash=0.1×SSC, 0.1% ×SDS, 40° C.). P. lophurae DNA may be removed from the hybridized DNA by methods well known in the art. More details of the hybridization protrol may be found in Kochan, supra.

Figure 1A:
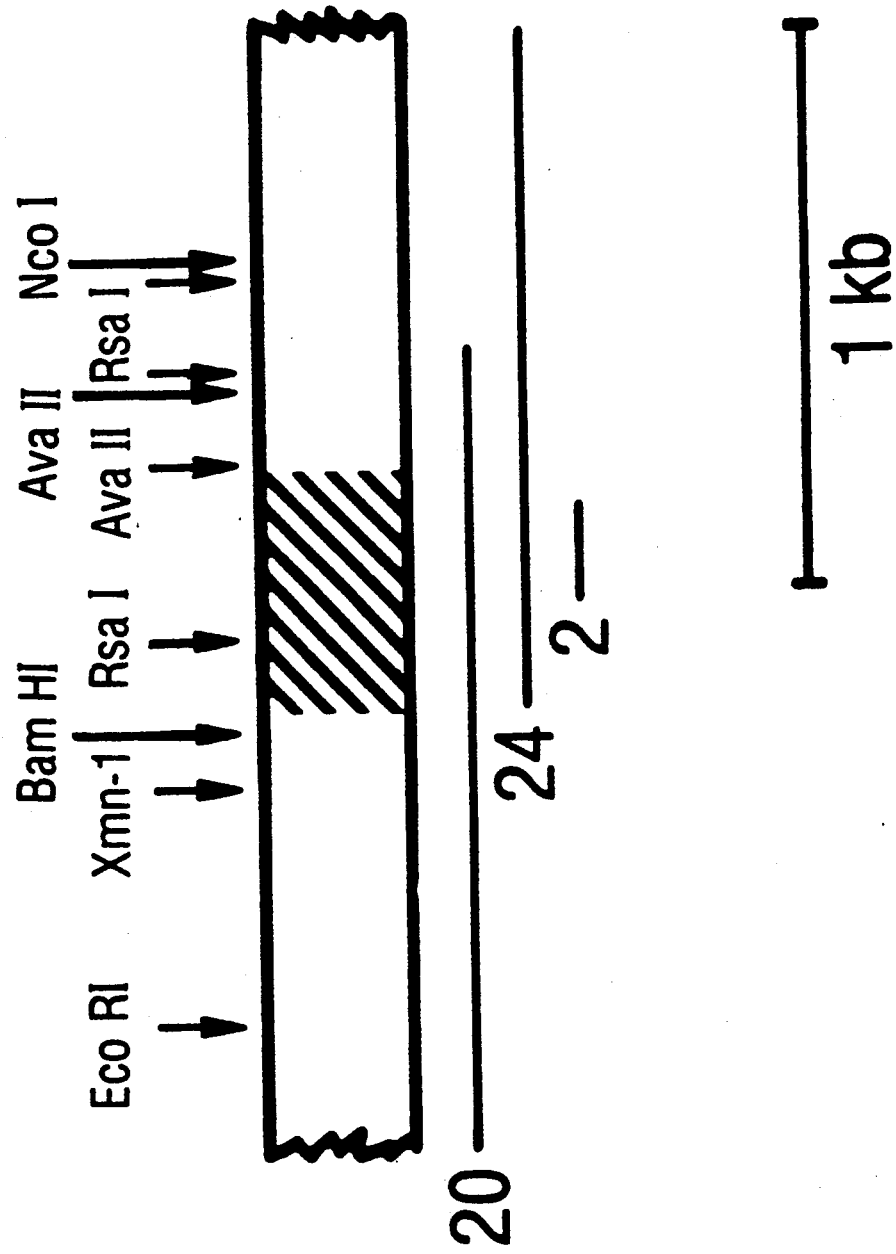
FIG. 1A depicts the restriction enzyme map of three clones of *P. falciparum* HisRP ($K^+$) expressing cDNA (1A).

The results of the hybridization protocol included three overlapping cDNA clones. These are depicted in FIG. 1A, and will be referred to as clones 2, 20, and 24. Restriction enzyme analysis, following methods known in the art, was used to obtain the restriction map shown in FIG. 1A. DNA sequence analysis, done following Maxam and Gilbert, Meth. Enzym. 65:499–560 (1980) (i.e., chemical degradation), gave additional characterization information. This information showed that the cDNA clones express an open reading frame with multiple polyhistidine sequences. These vary in length between 6-9 contiguous histidine residues. The contiguous histidine residue sequence represents a primary structure analogous to the *P. lophurae* histidine rich protein gene (Ravetch et al, supra). The histidine encoding sequence is shown by the hatched portion of FIG. 1A.

Fragment size was verified by performing co-migration experiments with genomic DNA, by methods known to the art and not repeated here. The analysis of the gene region shown has found no intervening sequences, within the limits of Southern blot analysis (Southern, *J. Mol. Biol.* 98:503-517 (1975) using cDNA and genomic fragments.

Characterization as Knobby (K+) or Knobless (K−) DNA

The cDNA clones which were produced as described, supra, were further characterized by restriction enzyme and Northern blot analysis to determine if they were knobby (K+) or knobless (K−$^H$) expressing DNA. This was done using K+ and K− RNA.

In these experiments, various strains of *P. falciparum* were grown in synchronous culture following Trager et al., *Science* 193:673-676 (1975), in order to obtain populations enriched in trophozoites or rings and schizonts. The strains grown are known to be either K+ or K−; FcR-3 is the non-clonal Gambian line described by Jensen et al.; *Am. J. Trop. Med. Hyg.* 33 534-537 (1978); A-2 is K+, while D-3, and D-4 are K−. These three strains are clonal derivatives of FcR-3 (Trager et al., *PNAS* 78:6527-6530 (1981). FVO+ is K+, derived from Vietnam isolate FcR-1/FVO (Trager et al., *Science* 193:673-675 (1976); FVO− is K− derived from FVO+ (-Gritzmacher et al., *Science* 226:65-67 (1984). CDC-1 is a K+ isolate (Bhasim et al., *Am. J. Trop. Med. Hyg.* 33:534-(1984), while T-26 is a K+ Tanzanian isolate.

After the various strains have been grown 1 g of their total RNA was fractionated on agarose-formaldehyde gels, transferred to nitrocellulose, and was hybridized with nick translated cDNA probes (with specific activity of $2 \times 10$ cpm/µg), these cDNA probes being identical to clones 20 (1.4/Kb), and clone 2 described supra. The hybridization was again performed under stringent conditions (50% formamide, 10% Dextran sulfate, 5 xssc, 7 mM TRIS, pH 7.6, 1 x Denhardts; 25 µg/ml salmon sperm DNA: final wash of 0.1SSC, 0.1% SDS at 52° C. In FIG. 1B, the results of hybridization experiments using clone 20 are shown, while in FIG. 1C, the corresponding experiments, using clone 2, are depicted. Size markers, as given in FIGS. 1B and C, are obtained from the *P. falciparum* and human RNA used in the given lanes.

Figure 1C:
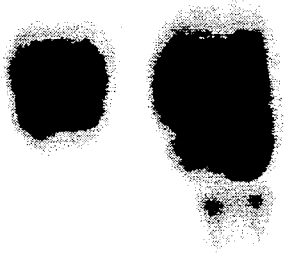
FIG. 1C depicts different stages of *P. falciparum* development.

The subtractive hybridization shown between K+ and K− clonal isolates (Henrick et al., *Nature* 308:149-153 (1984), shows that a stable mRNA transcript of about 4.2 kilobases accumulates in K+, but not K− clonal isolates. Maximal expression occurs in trophozoites (All of the lanes in FIG. 1B represent trophozoites; row "T" in FIG. 1C represents trophozoites also; R represents "rings," while "S" represents "schnizonts." Although not apparent from the figure, a faint band does appear in S, probably because of contamination with trophozoites). The expression pattern is in agreement with Vernot-Hernandez et al., *Mol. and Biochem. Parasitol* 12:337-350 (1984), who described an expression pattern of K+ histidine rich protein.

It is apparent from the data that a histidine rich amino acid DNA sequence is being expressed in K+, but not K− isolates. Geographic isolation appears to have no bearing on the expression of the gene (i.e., the gene is conserved). The clones therefore can be said to represent cDNA expressing a knob-associated histidine rich protein gene. This is referred to hereafter as the KAHRP gene.

Investigation of Loss of Gene in K− Isolates

As it is clear from the second experiment that stable transcripts of KAHRP (i.e., K+ mRNA) have been lost in K− clones, the mechanism underlying this loss was studied.

In this study, native DNA was isolated from the same strains described supra. HindIII was used to digest the DNA from FcR-3, D-4, FVO+, and FVO−. These were probed with a 5' Pst-EcoRI 250 base pair fragment of clone 20. DNA of FcR-3, A2, D-3, D-4, and FVO−− was digested with XmnI, and was then probed with the PstI 1.4 kb probe of clone 20, described supra using the same conditions.

Only a single hybridization fragment is detected for HindIII digestion, while two fragments are found following XmnI digestion, as is expected.

Figure 2B:
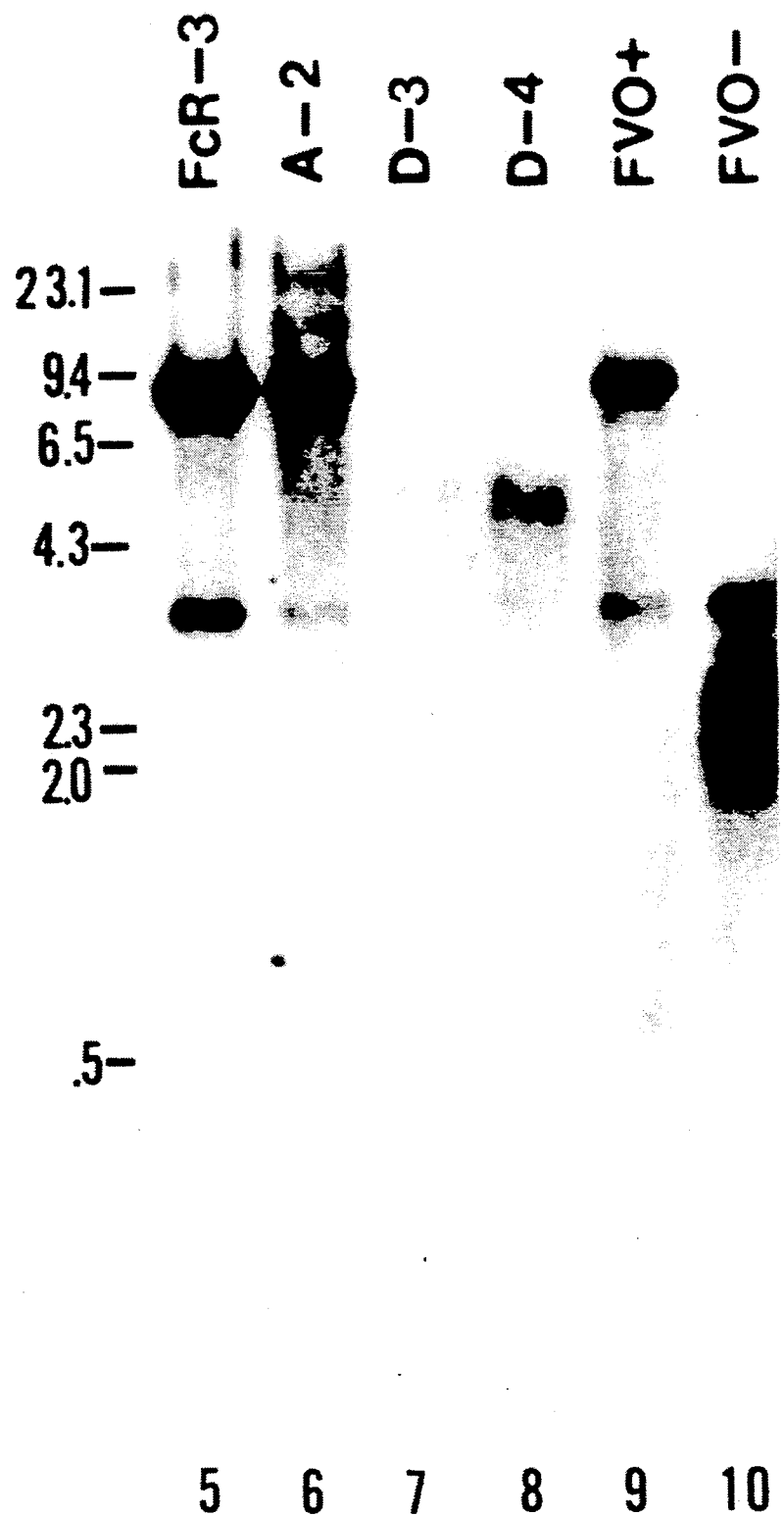
FIG. 2A and 2B shows the result of hybridization experiments using both $K^+$ and $K^-$ HisRP radiolabelled cDNA. A restriction map of the entire *P. falciparum* HisRP gene is shown as well (FIG. 2c).
Figure 2C:
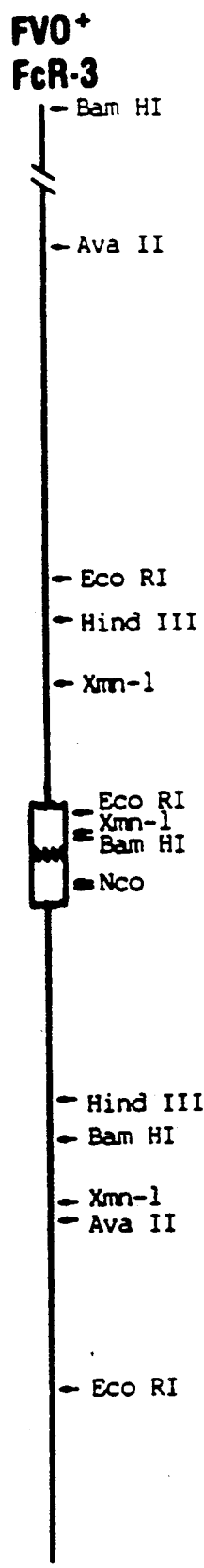
Figure 3A:
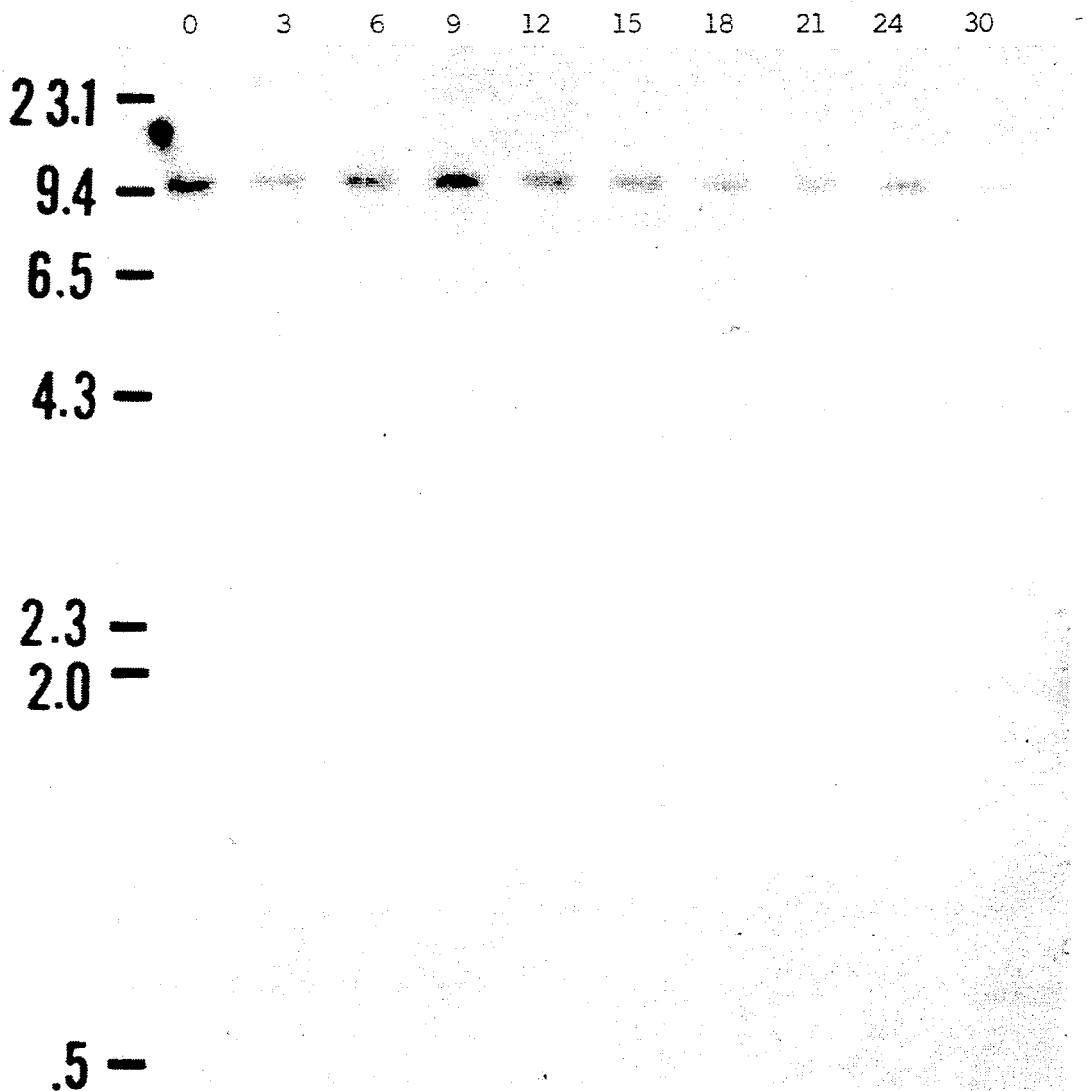
FIG. 3A and 3B shows the results of hybridization experiments following Bal 31 digestion. Restriction maps for both $K^+$ and $K^-$ strains are shown in FIG. 3C.
Figure 3C:
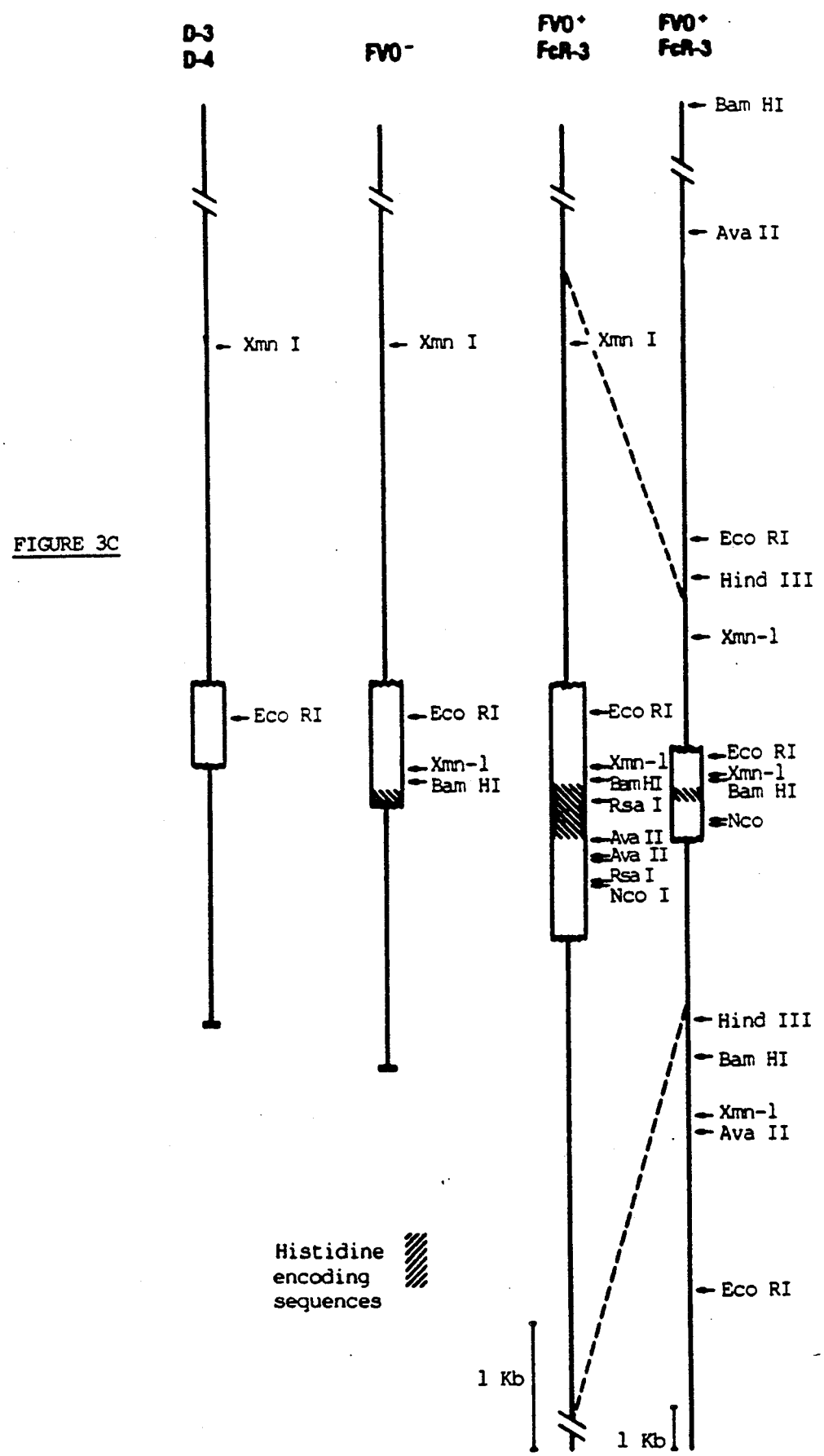

FIGS. 2A, 2B, and 2C shows that restriction fragments expressing K+ cDNA are conserved in K+ parasites and their derivatives. The Figure shows that a single HindIII fragment of 10.5 kb is detected by the labeled cDNA in K+ strains (lanes 1, 3) while two fragments are found following XmnI digestion (8.1 kb, 3.4 kb) (lanes 5, 6, 9). An internal XmnI site is present in the cDNA clone used (clone 20), which explains the two band pattern. Similar studies were performed on K+ isolates for Honduras (CDC-1) and Tanzania (T-26) strains, which are both K+. These additional studies reveal that the KAHRP gene is conserved.

The study also shows, however, that a DNA rearrangement has occurred in K− isolates. It is noted, for example, that the HindIII fragment in K− D-4 is 6.1 kb, while it is 7.2 kb in K− FVO−. Additionally, while the XmnI $5^1$ fragment, which encodes the polyhistidine sequence, now migrates as a diffuse $2.3 \pm 0.25$ kb band (lane 10). The K− isolates D-3 and D-4 have lost the $5^1$ XmnI site, resulting in a single rearranged XmnI fragment of 5.2 kb (lanes 7, 8). This rearrangement has resulted in deletion of DNA sequences corresponding to the 3' coding region of this gene.

III. Mapping of the K+

Restriction enzyme mapping of the strains shown in FIG. 2C with EcoRI, Bam HI, XmnI, AvaII and HindIII, singly and in combination, using probes derived to both the 5' and 3' sequences of this histidine-rich protein gene demonstrated that the break point of the deletion is different K− isolates varies by several hundred nucleotides. For clones D-3 and D-4, derived from FcR-3, the deletion break point results in the loss of all histidine encoding sequences, while in FVO−, derived from a Vietnam isolate, the break point retains polyhistidine sequences. The rearranged DNA fragment observed in these K− isolates is observed to migrate as a diffuse band, as seen in FIGS. 2A and 2B, lanes 2, 4, 7, 8, 10, implying that the DNA fragment which is generated is heterogenous with respect to length in the K− isolates. In addition, from these restriction mapping studies, a clustering of restriction enzyme cleavage sites appears to have been introduced 3' of this gene in K− isolates.

Sequence of K+ *P. FALCIPARUM cDNA*

Following methods well known in the art the K+ cDNA depicted by the restriction map of FIG. 1A, was sequenced, and an amino acid sequence expressed by the cDNA deduced. Both of these are shown in FIGS. 4A, 4B, 4C, and 4C. The nomenclature used to depict the amino acid sequence is one familiar to those skilled in the art, as will be seen in, e.g., Lehninger, *Biochemistry, Second Edition*, pp. 73–75 (Worth Publishers, Inc., New York, 1975). The cDNA is characterized by an open reading frame starting at position 640, and terminating at position 1846. The peptide is characterized by a histidine-rich region.

The cDNA described supra, was used in experiments designed for further analysis. cDNA clones were inserted into plasmid AS1 (Schatzman et al), which were transformed into *E. coli* strain AR15. A fusion protein was recovered after heat induction which was then used to induce production of antibodies in rabbits. Antibodies thus produced by the immunization, performed by standard methods, were found to be specific to the K+ protein, especially the BamNCO - AvaII restriction fragment, as shown in FIGS. 1A, 1B and 1C. This region includes the histidine-rich region of the peptide.

The antiserum thus produced will be seen to be useful, e.g., in assays to determine if an individual is infected with K− *P. falciparum.*

Column chromatography may be used, e.g., with purified antibodies being used for the specificity for the K+ protein.

Due to the similarity between K+ and K− parasites, one skilled in the art will see the efficacy of the K− parasite in producing a vaccine against malarial infection. K− *P. falciparum* are not implicated with the symptoms of the disease. Hence, K− parasite in, e.g., etiolated form, may be administered to a subject as protective immunogen. Antibodies produced in response would be expected to bind and inactivate K+ parasite.

The advantages of this invention will be readily apparent to one skilled in the art. Of particular interest is the availability of a new technique for diagnosis, or determining the presence of malaria. Falkow, et al., in U.S. Pat. No. 4,358,535, e.g., describe the use of DNA probes to determine the presence of complementary DNA in a sample. Hybridization probes for determining the presence of specific parasites has been taught by, e.g., P. Sloof, et al., *J. Mol. Biol.* 167:1:21 (1983) (*T. brucei* and *T. cruzi*); Barer, et. al., *Mol. & Biochem. Parasitol* 3:33–46 (1981), (*Leishmanio*); Arnot et al., *Mol. & Biochem. Parasitol* 3:47–56 (1981) (*L. tropica major; L. aethropia*); Borst, et al., *Biochim et. Biophys. Acta* 610:197–210 (1980) (*T. brucei*). It has never before been taught, however, that, via interspecies hybridization, P. falciparum may be diagnosed using a non-infective strain of Plasmodia, such as *P. lophurae.* This eliminates the dangers involved in the expected method of diagnosis, which would be the use of labelled *P. falciparum* DNA to determine infection in a human. By using, e.g., the protocol described infra, in vitro diagnosis, may be accomplished.

The terms and expression which have been employed are used as terms of description and not of limitation and there is no intention in the use of such terms and expressions of excluding any equivalents of the features shown and described or portions thereof, it being recognized &hat various modifications are possible within the scope of the invention.

We claim:

1. cDNA, expressing histidine-rich proteins of plasmodium falciparum associated with knob phenotype characterized by the nucleotide sequence of FIGS. 4A, 4B, 4C, and 4D.

2. cDNA of claim 1, characterized by the restriction map (FVO+) of FIG. 3C.

3. Substantially pure *P. falciparum* histidine-rich protein characterized by amino acid sequence:

```
MKS FKNKNTL RRKKAFDVFT
KIL LVSFLVWVLKCS NNCNN
GNGSGDSFDF RNKRTLAQKQ
HEHHHHHHQHQHQHQAPHQ
AHHHHHHGEVNHQAP QVHQQ
VHGQDQAHHHHHHHHHQLQP
QQL QGTVANP PSNEP VVKTQ
VFREARPGGGFKAYEEKYES
KHYKLKENVVDGKKDCDEKY
EAANYAFSEECPYTVNDYSQ
ENGPNI FALRKRFPLGMNDE
DEEGKEALAI KDKLPGGLDE
YQNQLYGI CNETCTTCGPAA
I        DYVPADAPNGYAYGG
SAHD
GSHGNLRGHGNKGS EGYGYE
APYNPGFNGAPGVMVCKLCP
TPWCRLFSSI RSSTWCSHGS
RYS SFSSVNKYGKHGDEKHH
SSK HEGNTVKEKKRKNQKN
TKTTMEKRKNQKNTKTMKMQ
KA
```

* * * * *